(12) United States Patent
Wang et al.

(10) Patent No.: US 6,584,165 B1
(45) Date of Patent: Jun. 24, 2003

(54) SCAN DATA CORRECTION VIEW WEIGHTING OF COMPUTED TOMOGRAPHIC IMAGES

(75) Inventors: Sharon X. Wang, Schaumburg, IL (US); Roy-Arnulf Helge Nilsen, Menomonee Falls, WI (US); John A. Fusco, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,400

(22) Filed: Jul. 10, 2002

(51) Int. Cl.⁷ .................................................. A61B 6/03
(52) U.S. Cl. .............................. 378/4; 378/15; 378/901
(58) Field of Search ........................... 378/4, 8, 15, 901

(56) References Cited

U.S. PATENT DOCUMENTS

| | | |
|---|---|---|
| 5,128,864 A | 7/1992 | Waggener et al. |
| 5,293,312 A | 3/1994 | Waggener |
| 5,307,264 A | 4/1994 | Waggener et al. |
| 5,384,912 A | 1/1995 | Ogrinc et al. |
| 5,528,704 A | 6/1996 | Parker et al. |
| 5,606,585 A * | 2/1997 | Hu ................. 378/15 |
| 6,215,561 B1 | 4/2001 | Kakutani |
| 6,256,038 B1 | 7/2001 | Krishnamurthy |
| 6,272,200 B1 | 8/2001 | Pan et al. |
| 6,341,154 B1 * | 1/2002 | Besson .................... 378/15 |
| 6,418,184 B1 * | 7/2002 | Wang et al. ............... 378/15 |
| 6,421,411 B1 * | 7/2002 | Hsieh ....................... 378/4 |
| 6,463,118 B2 * | 10/2002 | Besson .................... 378/15 |

* cited by examiner

*Primary Examiner*—David V. Bruce
(74) *Attorney, Agent, or Firm*—Carl B. Horton, Esq.; Armstrong Teasdale LLP; Thomas M. Fisher, Esq.

(57) ABSTRACT

One aspect of the present invention is a method for reconstructing computed tomographic (CT) images. The method includes generating a plurality of projection data, calculating a plurality of base weights using the projection data for each series of images to be reconstructed, storing the base weights in an external memory, and applying a z-smoothing module to the base weights to determine a plurality of final weights. The view weighting process then includes applying the final weights to the projection data for each image.

25 Claims, 3 Drawing Sheets

SCAN DATA CORRECTION VIEW WEIGHTING OF COMPUTED TOMOGRAPHIC IMAGES

BACKGROUND OF INVENTION

This invention relates generally to computed tomographic (CT) image generation, and more particularly to methods and apparatus for view weighting of CT image data.

Scan data correction plays an important role in the improvement of image quality. The final step of one scan data correction (SDC) process is a view weighting process and often is referred to as SDC-post.

At least one known view weighting process calculates the weights in real time, i.e., during the view weighting process. The performance of this known view weighting process is less than desirable, because calculating the weights requires too much time. Then, because the view weighting process is too slow, the whole image reconstruction process also is too slow. For example, the image reconstruction time exceeds 0.5. seconds for most modes of a four-slice scanner. The image reconstruction time is even greater where the known view weighting process is applied for an eight-slice scanner. Furthermore, the known z-smoothing module is blended into individual view weighting algorithms. Such blending not only complicates the software implementation, but sometimes can result in an incorrect z-smoothing mode.

SUMMARY OF INVENTION

In one aspect, a method is provided for generating computed tomographic (CT) images. The method includes generating a plurality of projection data, calculating a plurality of base weights using the projection data, storing the base weights in a memory, and applying a z-smoothing module to the base weights to determine a plurality of final weights.

In another aspect, a computer is provided for determining and storing a plurality of weights for each series of images to be reconstructed. In one embodiment, the computer includes a plurality of processors operating in parallel. The computer is programmed to generate a plurality of projection data, to calculate a plurality of base weights using the projection data, to store the base weights in a memory, and to apply a z-smoothing module to the base weights to determine a plurality of final weights.

In a further aspect, a computer-readable medium is provided that instructs a computer to determine and store a plurality of weights for each series of images to be reconstructed. The computer-readable medium instructs the computer to generate a plurality of projection data, to calculate a plurality of base weights using the projection data, to store the base weights in a memory, and to apply a z-smoothing module to the base weights to determine a plurality of final weights.

DETAILED DESCRIPTION

In some known CT imaging system configurations, a radiation source projects a fan-shaped beam which is collimated to lie within an X-Y plane of a Cartesian coordinate system and generally referred to as an imaging plane. The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a view. A scan of the object includes a set of views made at different gantry angles, or view angles, during one revolution of the radiation source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called CT numbers or Hounsfield units, which are used to control the brightness of a corresponding pixel on a display device.

To reduce the total scan time, a helical scan may be performed. To perform a helical scan, the patient is moved while the data for the prescribed number of slices is acquired. Such a system generates a single helix from a one fan beam helical scan. The helix mapped out by the fan beam yields projection data from which images in each prescribed slice may be reconstructed.

As used herein, an element or step recited in the singular and preceded with the word a or an should be understood as not excluding plural said elements or steps, unless such exclusion is explicitly recited. Furthermore, references to one embodiment of the present invention are not intended to be interpreted as excluding the existence of additional embodiments that also incorporate the recited features.

Also as used herein, the phrase reconstructing an image is not intended to exclude embodiments of the present invention in which data representing an image is generated but a viewable image is not. However, many embodiments generate (or are configured to generate) at least one viewable image.

Figure 1:
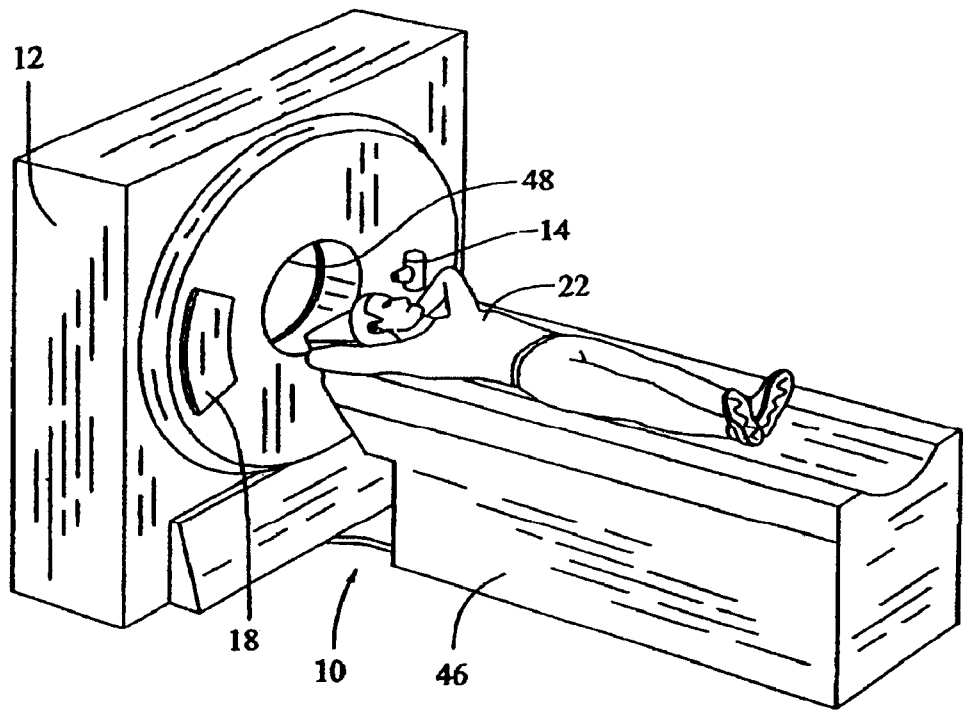
FIG. 1 is a pictorial view of a CT imaging system embodiment.
Figure 2:
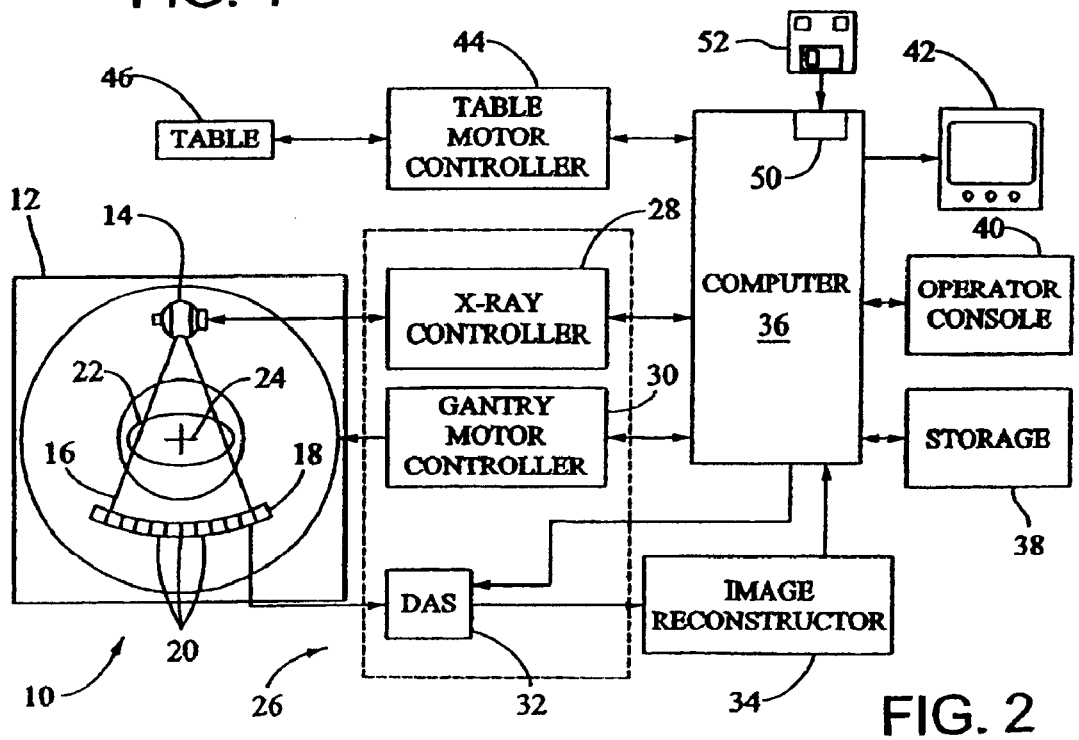
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a third generation CT imaging system. Gantry 12 has a radiation source 14 that projects a cone beam 16 of X-rays toward a detector array 18 on the opposite side of gantry 12. In one embodiment, radiation source 14 is a two-dimensional radiation source that projects a plurality of cone beams 16 from a plurality of locations on radiation source 14, also referred to herein as spots, on radiation source 14, toward detector 18 such that an inverted-cone beam geometry is received by detector 18.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes an radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28 and gantry motor. controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
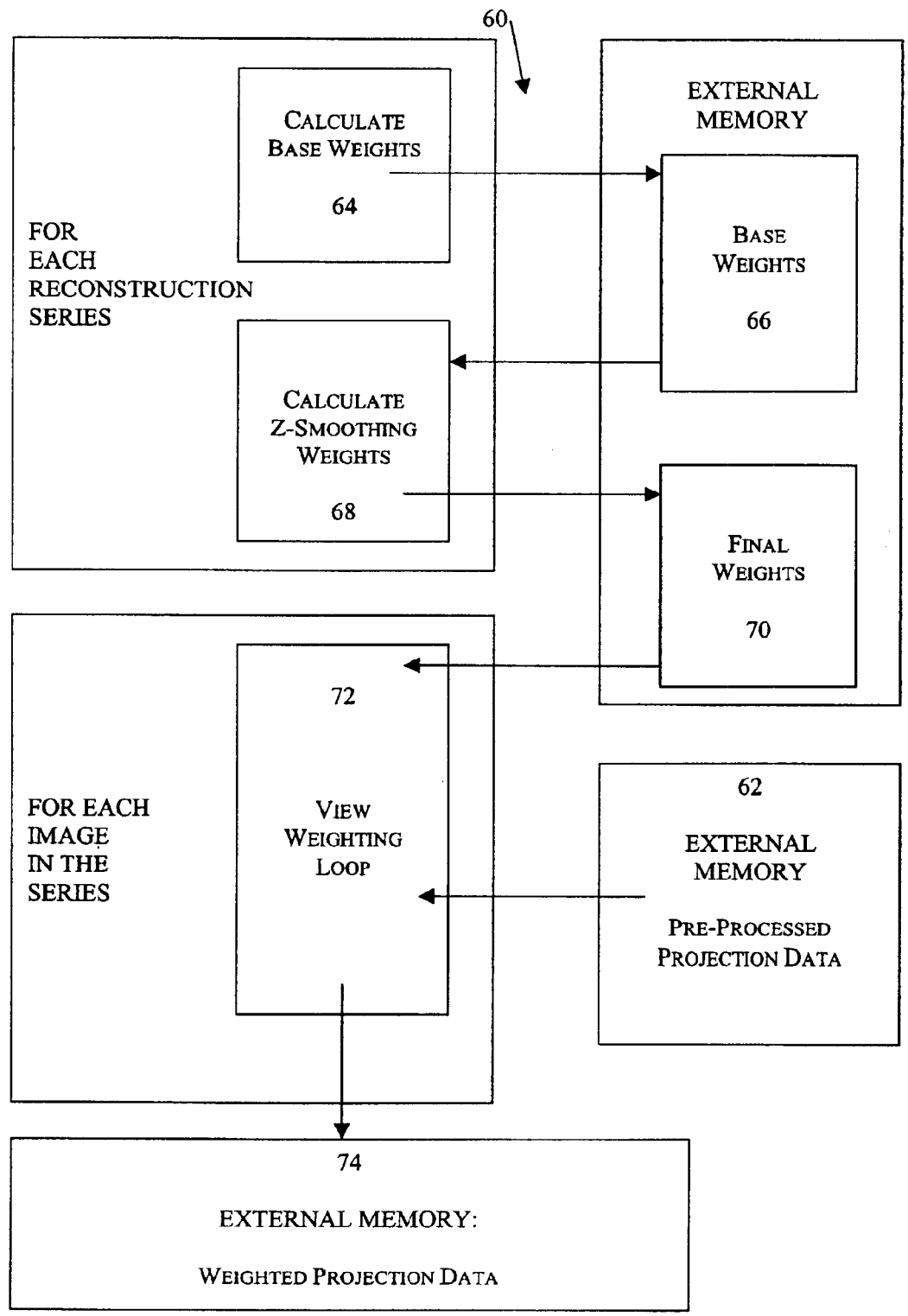
FIG. 3 is a flow diagram of a method for weighting projection data.

FIG. 3 is a flow diagram of a method 60 for view weighting projection data. In the exemplary embodiment, projection data is pre-processed to prepare scan data for view weighting and image generation. The projection data is then stored in an external memory 62. For each series of images to be reconstructed, a plurality of base weights are calculated 64 and stored in an external memory 66. Then the base weights are acquired by a z-smoothing module 68, which calculates a plurality of final weights, which are applied to the data. The final weights are stored in an external memory 70. Next, for each image in the reconstruction series, the final weights are obtained from external memory 70, the pre-processed projection data is obtained from external memory 62, and a view weighting loop 72 is initiated. In the exemplary embodiment, view weighting loop 72 includes exactly one multiplication and one summation, and the view weighting is accomplished efficiently in a relatively short time frame. The weighted projection data is then output to an external memory 74 and is used to reconstruct an image of the object.

Although external memories 62, 66, 70 and 72 are described as external to the processor performing the above described method, it is contemplated that the benefits of the invention accrue to processors that use an internal cache memory to store base weights and/or final weights. Further, in alternative embodiments, view weighting loop 72 includes multiple multiplications and/or multiple additions.

Figure 4:
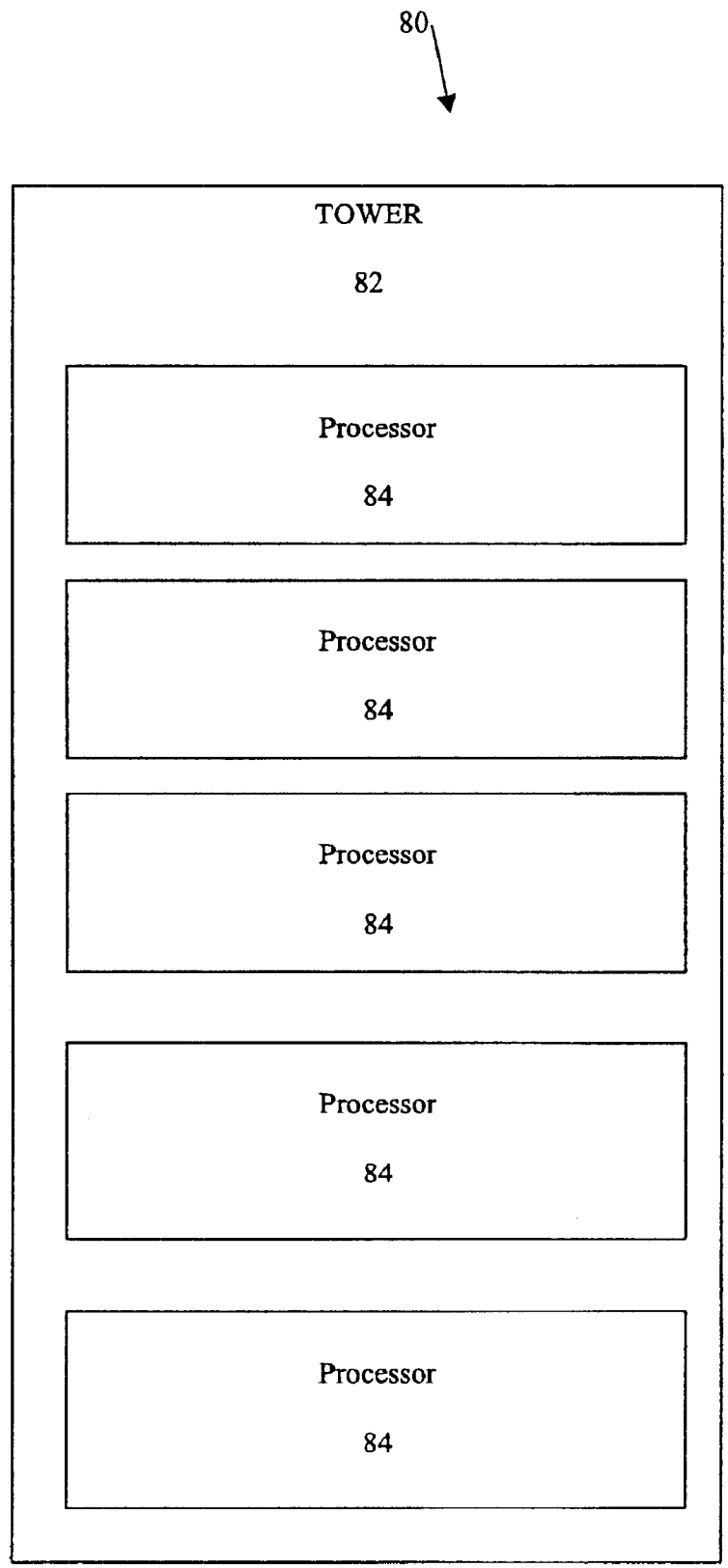
FIG. 4 is a block diagram representing an exemplary embodiment of a hardware platform.

FIG. 4 is a block diagram representing an exemplary embodiment of a hardware platform. Hardware platform 80 is part of image reconstructor 34. Hardware 80 includes a plurality of towers 82, each of which includes five processors 84 operating in parallel. Four of the five processors are used for pre-processing and one is used for view weighting. The view weighting process runs on a digital signal processor (DSP) with 64 MB external memory. Although using the above described hardware configuration has empirically shown to be efficient and cost effective, it is contemplated that the benefits of the invention accrue to hardware platforms which have more or fewer than five processors operating in parallel.

Embodiments of the present invention provide a significant reduction in time required for the view weighting process. Because calculating the weights consumes more than 60% of the total time necessary for the known view weighting process, pre-calculating the weights and storing them in a dynamic random access memory (DRAM) improves performance significantly. More specifically, the present invention enables all modes to accomplish the view weighting process in fewer than 0.5 seconds. Further, embodiments of the present invention provide improved slice sensitivity profile.

While the invention has been described in terms of various specific embodiments, those skilled in the art will recognize that the invention can be practiced with modification within the spirit and scope of the claims.

What is claimed is:

1. A method for generating computed tomographic (CT) images, said method comprising:
   generating a plurality of projection data;
   calculating a plurality of base weights using the projection data;
   storing the base weights in a memory; and
   applying a z-smoothing module to the base weights to determine a plurality of final weights.

2. A method in accordance with claim 1 further comprising determining the final weights for each of a plurality of series of images.

3. A method in accordance with claim 1 further comprising applying the final weights to the projection data to generate a plurality of CT images.

4. A method in accordance with claim 1 further comprising applying the final weights to a plurality of pre-processed projection data.

5. A method in accordance with claim 1 further comprising applying the final weights to a plurality of pre-processed projection data using one multiplication and one summation.

6. A method in accordance with claim 1 further comprising storing the final weights in a memory.

7. A method in accordance with claim 4 further comprising storing a plurality of weighted projection data for each of a plurality of images in a memory.

8. A computer programmed to generate computed tomographic (CT) images, said computer programmed to:
  generate a plurality of projection data;
  calculate a plurality of base weights using the projection data;
  store the base weights in a memory; and
  apply a z-smoothing module to the base weights to determine a plurality of final weights.

9. A computer in accordance with claim 8 further programmed to determine the final weights for each of a plurality of series of images.

10. A computer in accordance with claim 8 further programmed to apply the final weights to the projection data to generate a plurality of CT images.

11. A computer in accordance with claim 8 further programmed to apply the final weights to a plurality of pre-processed projection data.

12. A computer in accordance with claim 8 further programmed to apply the final weights to a plurality of pre-processed projection data using one multiplication and one summation.

13. A computer in accordance with claim 8 further programmed to store the final weights in a memory.

14. A computer in accordance with claim 11 further programmed to store a plurality of weighted projection data for each of a plurality of images in a memory.

15. A computer-readable medium encoded with a computer program, said program configured to:
  generate a plurality of projection data;
  calculate a plurality of base weights using the projection data;
  store the base weights in a memory; and
  apply a z-smoothing module to the base weights to determine a plurality of final weights.

16. A computer-readable medium in accordance with claim 15 where said program is further configured to instruct the computer to determine the final weights for each of a plurality of series of images.

17. A computer-readable medium in accordance with claim 15 where said program is further configured to apply the final weights to the projection data to generate a plurality of CT images.

18. A computer-readable medium in accordance with claim 15 where said program is further configured to apply the final weights to a plurality of pre-processed projection data.

19. A computer-readable medium in accordance with claim 15 where said program is further configured to apply the final weights to a plurality of pre-processed projection data using one multiplication and one summation.

20. A computer-readable medium in accordance with claim 15 where said program is further configured to store the final weights in a memory.

21. A computer-readable medium in accordance with claim 18 where said program is further configured to store a plurality of weighted projection data for each of a plurality of images in a memory.

22. A computed tomographic (CT) imaging system for reconstructing an image of an object, said imaging system comprising:
  a detector array;
  at least one radiation source; and
  a computer coupled to said detector array and said radiation source, said computer configured to:
    generate a plurality of projection data;
    calculate a plurality of base weights using the projection data;
    store the base weights in a memory; and
    apply a z-smoothing module to the base weights to determine a plurality of final weights.

23. A computer in accordance with claim 22 further programmed to determine the final weights for each of a plurality of series of images.

24. A computer in accordance with claim 22 further programmed to apply the final weights to the projection data to generate a plurality of CT images.

25. A computed tomographic (CT) imaging system for reconstructing an image of an object, said imaging system comprising:
  a detector array;
  at least one radiation source; and
  a computer coupled to said detector array and said radiation source, said computer configured to:
    generate a plurality of projection data;
    calculate a plurality of base weights using the projection data;
    store the base weights in a memory;
    apply a z-smoothing module to the base weights to determine a plurality of final weights; and
    apply the final weights to a plurality of pre-processed projection data using one multiplication and one summation.

* * * * *